(12) United States Patent
Schweikert (10) Patent No.: US 8,752,314 B2
(45) Date of Patent: Jun. 17, 2014

(54) CATHETER INFORMATION RING

(75) Inventor: Timothy Schweikert, Levittown, PA (US)

(73) Assignee: Medical Components, Inc., Harleysville, PA (US)

( * ) Notice: Subject to any disclaimer, the term of this patent is extended or adjusted under 35 U.S.C. 154(b) by 940 days.

(21) Appl. No.: 10/950,999

(22) Filed: Sep. 27, 2004

(65) Prior Publication Data

US 2005/0044759 A1 Mar. 3, 2005

Related U.S. Application Data

(62) Division of application No. 10/264,780, filed on Oct. 4, 2002, now Pat. No. 6,823,617.

(60) Provisional application No. 60/327,514, filed on Oct. 5, 2001.

(51) Int. Cl.
*G09F 3/16* (2006.01)

(52) U.S. Cl.
USPC .............................. 40/299.01; 40/316; 40/666

(58) Field of Classification Search
USPC .............. 40/299.01, 316, 317, 322, 334, 660, 40/666; 24/339, 459, 543, 563, 597; 174/112; D13/157; 251/9, 10
See application file for complete search history.

(56) References Cited

U.S. PATENT DOCUMENTS

| | | | |
|---|---|---|---|
| 2,894,056 A * | 7/1959 | Bogese | ............................ 174/92 |
| 3,068,600 A | 12/1962 | Blanchet | |
| 4,256,132 A | 3/1981 | Gunter | |
| 4,378,648 A | 4/1983 | Loof et al. | |
| 4,497,124 A | 2/1985 | Olive | |
| 4,775,121 A | 10/1988 | Carty | |
| 5,138,784 A | 8/1992 | Niwa | |
| 5,203,056 A | 4/1993 | Funk et al. | |
| 5,281,228 A | 1/1994 | Wolfson | |
| 5,309,604 A | 5/1994 | Poulsen | |
| 5,316,246 A | 5/1994 | Scott et al. | |
| 5,334,955 A * | 8/1994 | Strnad | ............................. 333/12 |
| 5,407,109 A | 4/1995 | Zuckerman | |

(Continued)

FOREIGN PATENT DOCUMENTS

| | | |
|---|---|---|
| CH | 683907 A5 | 6/1994 |
| DE | 883005 | 7/1949 |
| WO | WO00/44422 | 8/2000 |

OTHER PUBLICATIONS

Supplementary European Search Report dated Nov. 8, 2006 in EP application No. 02784025.5-2214 (4 pages).

(Continued)

*Primary Examiner* — Gary Hoge
(74) *Attorney, Agent, or Firm* — Glenn M. Massina, Esq.; Fox Rothschild LLP (57) ABSTRACT

An information ring for use with a catheter is disclosed. The information ring includes a body having a first end and a second end. The body has a first body face extending between the first end and the second end, and a second, generally convex face extending between the first end and the second end. The body has an opening extending therethrough between the first body face and the second face. A first indicia portion is located at the first end. The first indicia portion has a first indicia face sized to allow indicia to be printed on the first indicia face.

19 Claims, 10 Drawing Sheets

(56) References Cited

U.S. PATENT DOCUMENTS

| | | |
|---|---|---|
| 5,950,883 A | 9/1999 | Bond et al. |
| 5,971,436 A | 10/1999 | Cox |
| 5,974,708 A | 11/1999 | Webb et al. |
| 6,089,527 A | 7/2000 | Utterberg |
| 6,335,672 B1 * | 1/2002 | Tumlin et al. ................. 336/175 |
| 6,823,617 B2 * | 11/2004 | Schweikert ................ 40/299.01 |

OTHER PUBLICATIONS

Office Action dated Aug. 26, 2008; Japanese Application No. 2003-533993 (10 pages).

* cited by examiner

CATHETER INFORMATION RING

CROSS-REFERENCE TO RELATED APPLICATION

This application is a division of application Ser. No. 10/264,780, filed 4 Oct. 2002, now U.S. Pat. No. 6,823,617 entitled CATHETER INFORMATION RING, which claims priority from U.S. Provisional Patent Application Ser. No. 60/327,514, filed Oct. 5, 2001.

BACKGROUND OF THE INVENTION

Catheters for the introduction or removal of fluids may be located in various venous locations and cavities throughout the body for the introduction or removal of such fluids. Such catheterization may be performed by using a single catheter having multiple lumens. A typical example of a multiple lumen catheter is a dual lumen catheter in which a first lumen introduces fluids and a second lumen removes fluids. These catheters are very useful for procedures such as hemodialysis, wherein blood is removed from a patient through the first lumen for processing in a hemodialysis machine, and the processed blood is returned to the patient through the second lumen. Alternatively, multiple catheters, each having a single lumen, may be inserted in multiple locations in the patient, such as in each femoral vein.

Catheters are manufactured in different sizes and from different materials depending on the circumstances of their use. For example, smaller catheters are used on smaller patients, and different materials may be used depending on whether the catheter is intended to be in the patient for a short period of time, such as several hours or days, or for an extended period of time, such as weeks or months.

Catheters typically include indicia printed on the extension tubes that provides vital information such as the size, priming volume, and recommended as well as contra-indicated cleaning solutions to use around the catheter entrance to the patient. For example, some cleaning fluids can actually dissolve certain types of polyurethane materials from which some catheters are constructed. Text information is placed on the extension tubes to warn the user not to use such cleaning fluids.

The information printed on the extension tubes may vary depending on the intended catheter use. However, one drawback to this approach is that text size and clarity is limited, since the extension tubes are tubular and are typically translucent. Additionally, the text applied to the extension tubes is susceptible to rubbing off over time. Further, information such as priming volume may be printed on the catheter, such as on the extension tube. If a repair is necessary that requires a luer to be removed and a new, replacement luer installed onto the extension tube, the priming volume has changed, because the extension tube has been shortened as a result of the luer replacement. It would be desirable to provide a replaceable component with the catheter that can indicate the correct priming volume after such a replacement.

Further, it would be desirable to provide a surface on a catheter on which important information may be printed which may be easily read by the user and which will not wear off during the life of the catheter. Further, it would be beneficial to provide an information ring that may be removed from a catheter, and a new information ring installed on the catheter without having to disassemble any other portion of the catheter.

BRIEF SUMMARY OF THE PRESENT INVENTION

The present invention provides an information-bearing article for use with tubing such as a medical catheter and may be used separately or in combination with a tubing clamp. In several embodiments, the information ring comprises a body having a first end and a second end, and further having a first body face extending between the first end and the second end, and a second, generally convex face extending between the first end and the second end. The body has an opening extending therethrough between the first body face and the second face. A first indicia portion is located at the first end. The first indicia portion has a first indicia face sized to allow indicia to be printed on the first indicia face.

The present invention also provides a conduit assembly. The conduit assembly includes a conduit having a first end and a second end and an information ring. The information ring includes a body having a first end and a second end. The body has a first body face extending between the first end and the second end, and a second, generally convex face extending between the first end and the second end. The body has an opening extending therethrough between the first body face and the second face. A first indicia portion is located at the first end. The first indicia portion has a first indicia face sized to allow indicia to be printed on the first indicia face. The assembly further includes a conduit clamp having first and second openings along an axis. The information ring is disposed such that the channel is along the axis between the first and second openings. The conduit extends through the first and second openings and the channel along the axis.

Also, the present invention provides a method of inserting an information ring onto a catheter assembly. The method comprises providing a conduit assembly comprising a conduit having a first end and a second end. A first fitting is connected to the first end and a second fitting is connected to the second end. The assembly further includes a conduit clamp adapted to releasably retain the information ring over the conduit. The conduit is disposed within an opening in the conduit clamp. The method further includes providing an information ring comprising a body having a first end and a second end. The body has a first body face extending between the first end and the second end, and a second, generally convex face extending between the first end and the second end. The body further has an opening extending therethrough between the first body face and the second face and a first indicia portion having a first face extending from the first end. The first indicia portion is sized to allow indicia to be printed on the first face. The method further comprises installing the information ring in the conduit assembly, such that the conduit is disposed within the opening and the conduit clamp releasably retains the information ring over the conduit.

Further, the present invention provides a catheter information ring. The ring comprises a first portion having a first connecting end and a first free end. The first connecting end includes at least one of a male connector and a female connector and the first free end has a first indicia face. The ring further comprises a second portion having a second connecting end and a second free end. The second connecting end has at least the other of a mating male connector and a mating female connector. The second free end has a second face. When the at least one of the male connector and the female connector is engaged with the at least one of the mating male connector and the mating female connector, a generally circular opening is formed in the ring such that a catheter conduit is sized to fit within the opening.

Additionally, the present invention comprises an information-bearing article for use with tubing such as medical catheters in combination with a clamp, to provide readily visible information relevant to the particular catheter. The article has a body with a first end and an opposed second end interconnected by an interconnecting section extending therebetween, and is adapted to be assembled within the clamp, as well as removable therefrom when the clamp is already in position along the catheter. Preferably, the article is of one-piece construction. When assembled within the clamp, the first and second ends are disposed along opposite sides of the clamp and catheter so that an outwardly-facing surface of at least one of the first and second ends bears indicia thereon; the interconnecting section does not impinge on the catheter and does not interfere with the clamp being manipulated between clamping and unclamping states.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings, the same reference numerals are employed for designating the same elements throughout the several figures. In the drawings.

DETAILED DESCRIPTION OF THE PRESENT INVENTION

In the drawings, like numerals indicate like elements throughout. Certain terminology is used herein for convenience only and is not taken to be a limitation on the present invention. The words "right", "left", "outwardly", and "inwardly" designate directions in the drawings to which reference is made. The words "proximal" and "distal" refer to directions away from and closer to, respectively, the insertion tip of a catheter in the catheter assembly described according to the present invention. The terminology includes the words above specifically mentioned, derivatives thereof, and words of similar import. The following describes preferred embodiments of the invention. However, it should be understood based on this disclosure that the invention is not limited by the preferred embodiments described herein.

Figure 1:
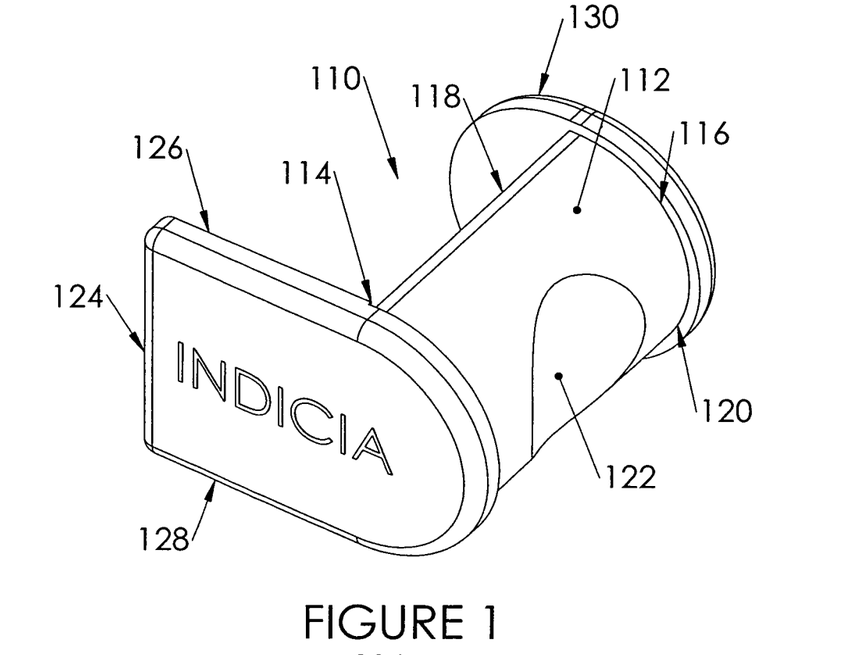
FIG. 1 shows a perspective view of an information ring according to a first embodiment of the present invention.
Figure 2:
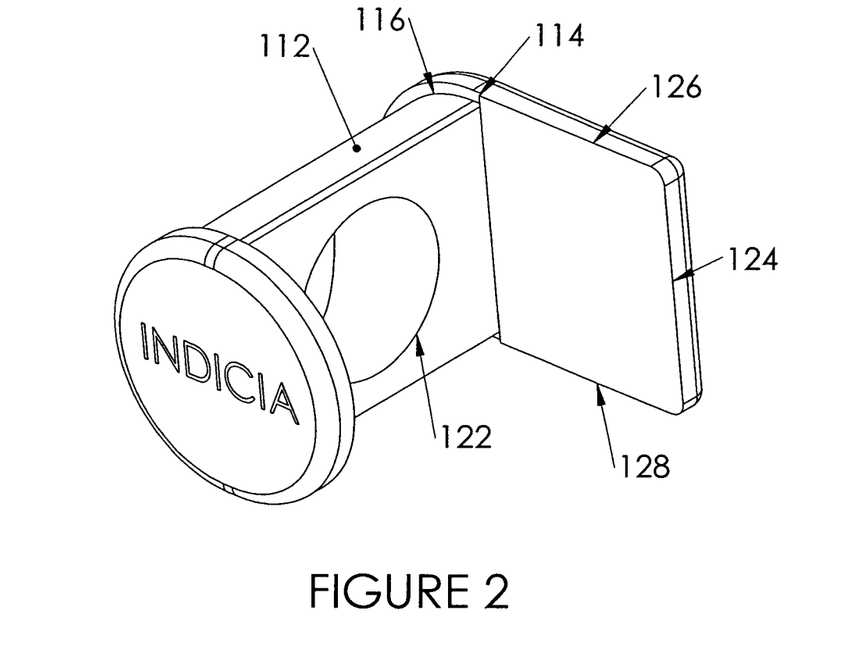
FIG. 2 shows an opposing perspective view of the information ring shown in FIG. 1.

A first embodiment of an information ring 110 for use with a catheter according to the present invention is shown in FIGS. 1 and 2. The information ring 110 includes a body 112 having a first end 114 and a second end 116. A generally planar first face 118 extends between the first end 114 and the second end 116. A second face 120, preferably generally rounded, extends between the first end 114 and the second end 116. A generally circular opening 122 extends through the body 112 between the first face 118 and the second face 120. A generally elongated first indicia portion 124, which is located at the first end 114 of the body 112, includes an indicia face 128, on which identifying indicia is printed. As can be seen from FIG. 1, the first indicia portion 124 extends generally orthogonally from the first face 118, although those skilled in the art will recognize that the first indicia portion 124 may extend other than orthogonally from the first face 118. A second indicia portion 130 is located at the second end 116 of the body 112 and includes an indicia face 132 on which identifying indicia is printed. The second indicia portion 130 preferably is generally round in shape, as shown in FIG. 2, but the second indicia portion 130 may have other shapes, such as a generally elongated shape similar to the first indicia portion 124.

Indicia, shown on indicia faces 128, 132 in FIGS. 1 and 2, respectively, may be printed in any direction, or along any curvature, as desired. Further, the indicia may be information such as priming volume and/or site care warnings about the use of the device to which the information ring 110 is attached. Further, indicia may include warnings related to the contents of the catheter or other general information related to the catheter. The types of indicia provided are for example only and are not meant to be limiting. Such information and/or site care warnings may be in the form of letters, numbers, symbols, colors, texture, and the like. Typically, the indicia is printed in a large enough font so that a user may easily read the information printed on the information ring 110.

Figure 3A:
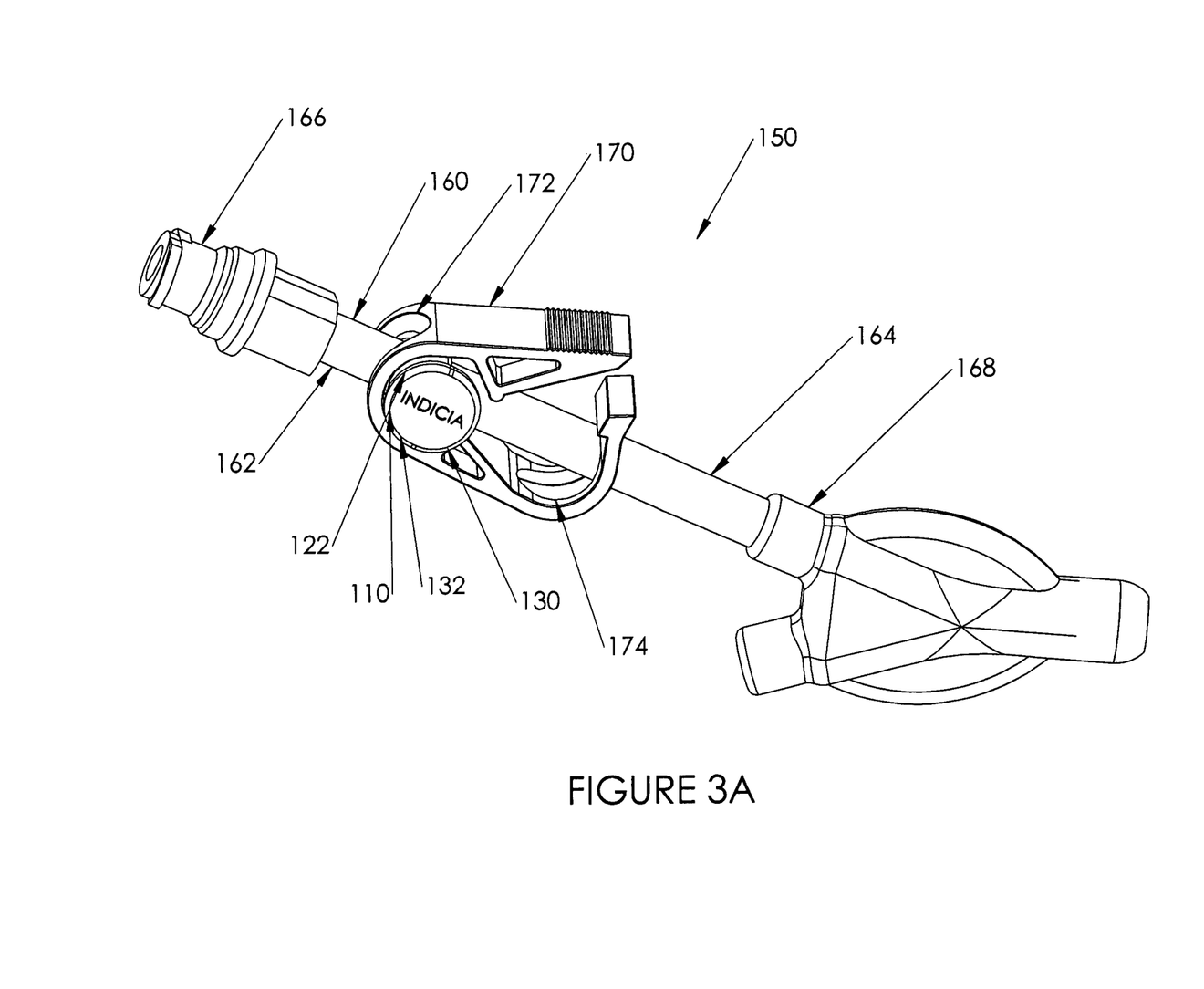
FIG. 3A shows a perspective view of information ring shown in FIGS. 1 and 2 connected to a catheter assembly.
Figure 3B:
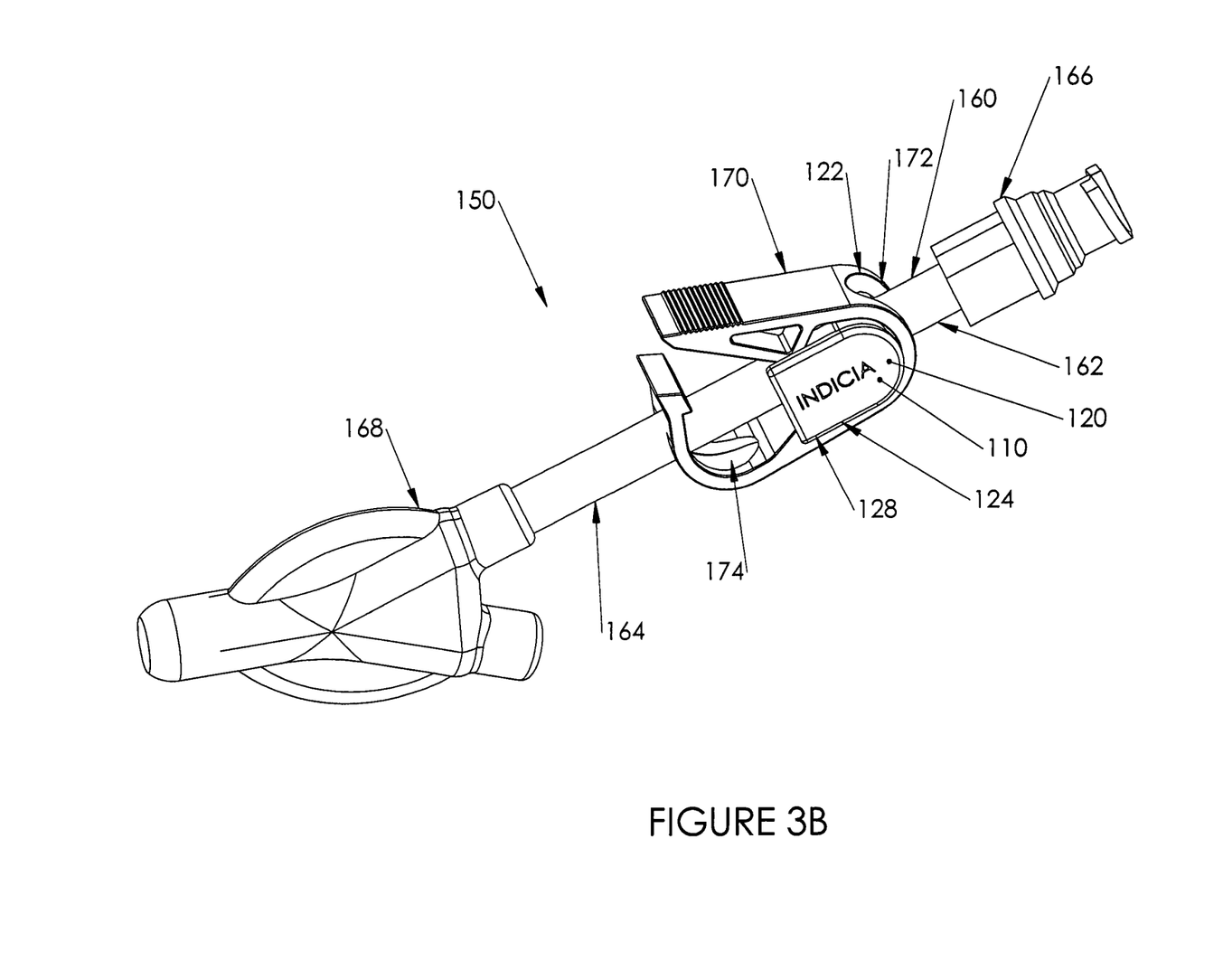
FIG. 3B shows an opposing perspective view of the information ring shown in FIGS. 1 and 2 connected to the catheter assembly.

The information ring 110 is part of a conduit assembly 150, which, for example, is part of a catheter assembly, such as that shown in FIG. 3. The conduit assembly 150 is comprised of the information ring 110; a conduit 160, such as a catheter extension tube; and a conduit clamp 170. The conduit assembly 150 is typically used for medical purposes including, but not limited to: catheters, intravenous (IV) solutions, high flow blood administration sets, irrigation/urology products, pharmaceutical products, fluid dispensing systems, chamber mixing bags, formulator systems, infusion systems, interventional products, fluid collection systems used in radiology, and other products and uses.

The conduit 160 is typically a catheter extension tube, which is located at the proximal end of the catheter. With some well known catheters, such as the ASH SPLITCAT® catheter, where the catheter assembly contains two separate conduits 160, one for removal of fluids from the patient, and the other for returning fluids to the patient, each conduit 160 is preferably provided with its own information ring 110. For clarity, only one conduit 160 with an information ring 110 is described herein.

As shown in FIGS. 3A and 3B, the conduit 160 has a first, or proximal, end 162 and a second, or distal, end 164. Typically, the first end 162 is connected to a connection device 166, such as a luer, as shown. The second end 164 is typically connected to a hub 168, as shown. Also as shown in FIGS. 3A and 3B, the conduit clamp 170 is a clamp well known in the art. The conduit clamp 170 has two generally elongated openings 172, 174, through which the conduit 160 extends, so that the conduit clamp 170 is retained on the conduit 160. Further, the conduit 160 passes through the opening 122 in the information ring 110 between the openings 172, 174 in the conduit clamp 170.

In order to remove the information ring 110 from the conduit 160, the conduit 160 is severed, such as by cutting. The conduit 160 is typically cut proximate the connection device 166, and the conduit 160 is pulled through the first opening 172 in the clamp 170 and the opening 122 in the information ring 110 so that the information ring 110 may be removed from the conduit assembly 150. A new information ring 110 is then provided, with the conduit 160 being pushed through the opening 122 in the new information ring 110 and the first opening 172 in the clamp 170. A new connection device 166 is then affixed to the conduit 160, securely locating the information ring 110 and the clamp 170 on the conduit 160 between the connection device 66 and the hub 168.

For the following second through fourth embodiments of the information-bearing article according to the present invention which is described hereafter in detail, like or similar elements are identified by a similar three-digit number with the last two digits being identical and corresponding to like or similar elements of a second embodiment 210. For the second embodiment, the first digit is a "2"; for the third embodiment, the first digit is a "3"; and for the fourth embodiment, the first digit is a "4". As may be discerned in FIGS. 4 and 5, the information-bearing article is so shaped and dimensioned, or adapted, for an interconnecting section between the first and second ends to extend transversely past the conduit or catheter and is adapted not to impinge thereon after assembly. The article is adapted to be inserted into the interior region of a clamp and more particularly may even be inserted into the clamp when the clamp is in position on the catheter, and may be removable therefrom when desired without first removing the clamp from the catheter. Preferably, the information-bearing article is of one-piece or unitary construction, as shown.

Figure 4:
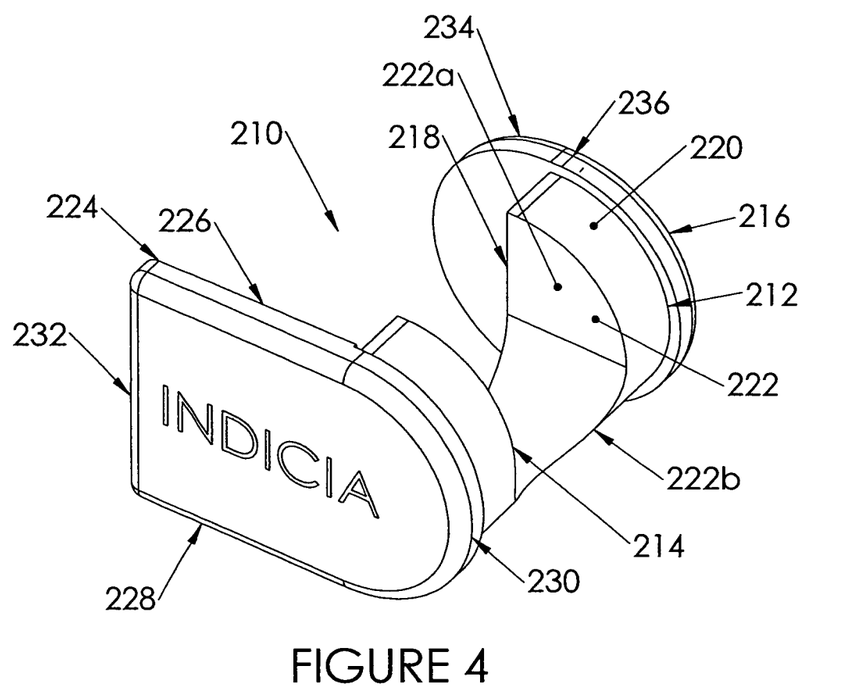
FIG. 4 shows a perspective view of an information ring according to a second embodiment of the present invention.
Figure 5:
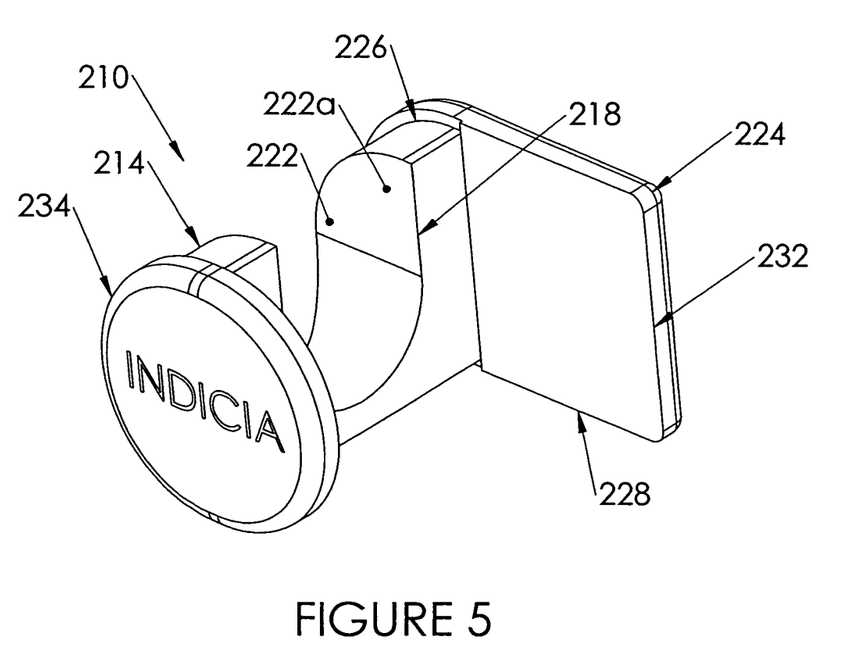
FIG. 5 shows an opposing perspective view of the information ring shown in FIG. 4.

A second embodiment of an information ring 210 according to the present invention is shown in FIGS. 4 and 5. The information ring 210 includes a body 212 having a first end 214 and a second end 216 interconnected by an interconnecting portion. A first face 218 of the interconnecting portion extends between the first end 214 and the second end 216. Preferably, the first face 218 is generally planar, although those skilled in the art will recognize that the first face 218 may be other than planar. A generally rounded second face 220 of the interconnecting portion extends between the first end 214 and the second end 216. A generally U-shaped channel 222 extends through the body 212 between the first face 218 and the second face 220. The channel 222 has an open portion 222a and a generally semi-circular closed portion 222b opposing the open portion 222a. A first indicia portion 224 is located at the first end 214 of the body 212, and includes an indicia face 228, on which identifying indicia is printed. The first indicia portion 224 has a first end 230 connected to the first end 214 of the body 212, and the first end 230 is preferably rounded, to complement the generally rounded second face 220 of the body 212. The first indicia portion 224 also has a second, free end 232 extending away from the body 212, and is preferably elongated in shape, although those skilled in the art will recognize that the free end 232 may be any shape. As shown in FIGS. 4 and 5, the first indicia portion 224 is generally disposed approximately orthogonally from the body 212, although those skilled in the art will recognize that the first indicia portion 224 may be disposed at other angles relative to the body 212.

A second indicia portion 234 is located at the second end 216 of the body 212, and includes an indicia face 236, on which identifying indicia is printed. As shown in FIGS. 4 and 5, the second indicia portion 234 has a radius that is preferably slightly larger than the radius of the second face 220. However, those skilled in the art will recognize that the radius of the second indicia portion 234 may be the same as or less than the radius of the second face 220.

Indicia, shown on indicia faces 228, 238 in FIGS. 4 and 5, respectively, may be printed in any direction, or along any curvature, as desired. Further, the indicia may be information such as priming volume and/or site care warnings about the use of the device to which the information ring 210 is attached. Further, the indicia may be warnings related to the contents of the catheter or other general information related to the catheter. The types of indicia provided are for example only and are not meant to be limiting. Such information and/or site care warnings may be in the form of letters, numbers, symbols, colors, texture, and the like. Typically, the indicia is printed in a large enough font so that a user may easily read the information printed on the information ring 210.

Figure 6:
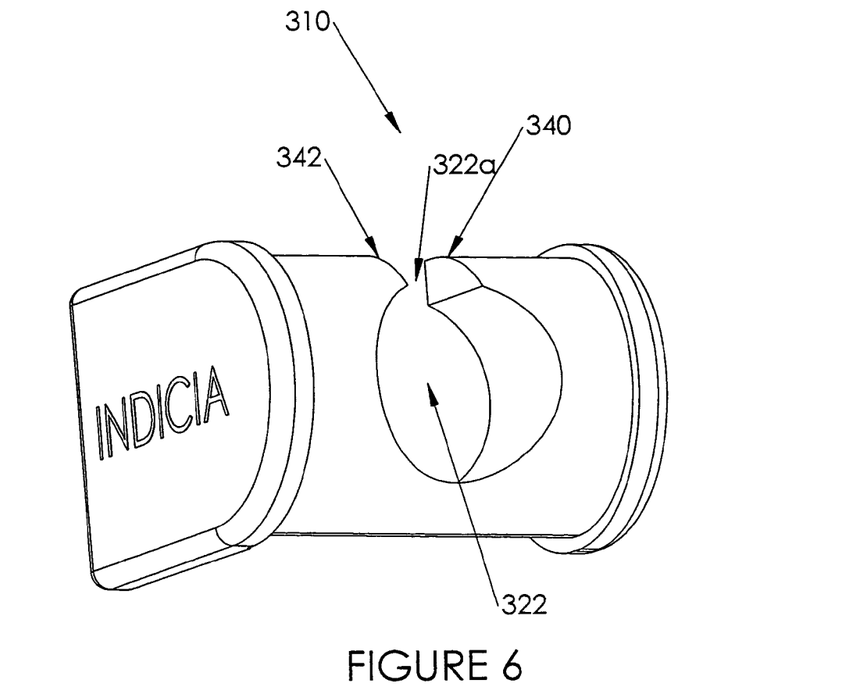
FIG. 6 shows a perspective view of an information ring according to a third embodiment of the present invention.
Figure 7:
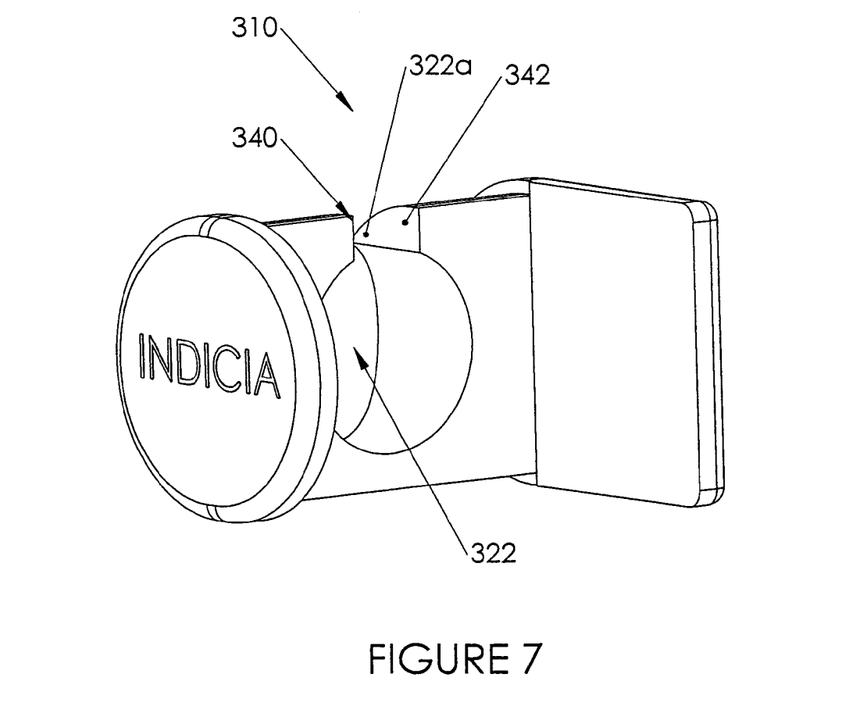
FIG. 7 shows an opposing perspective view of the information ring shown in FIG. 6.

A third embodiment of an information ring 310 according to the present invention is shown in FIGS. 6 and 7. The information ring 310 is similar to the information ring 210 as described above, but with a pair of tabs 340, 342 that extend from the body 312 toward each other partially across the open portion 322a of the channel 322. Although two tabs 340, 342 are shown, those skilled in the art will recognize that only one tab 340 need be used.

Figure 8:
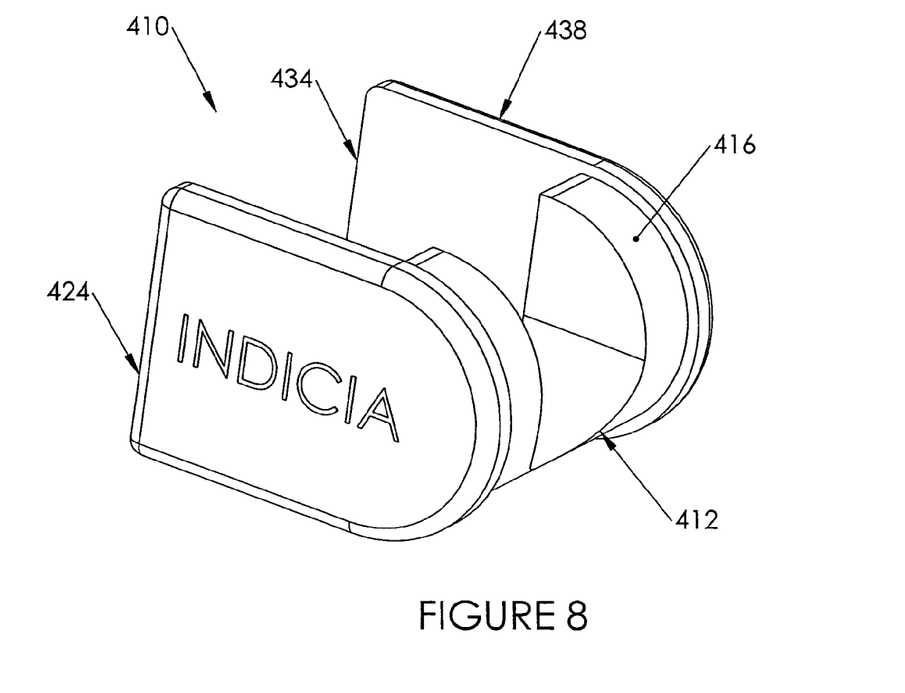
FIG. 8 shows a perspective view of an information ring according to a fourth embodiment of the present invention.
Figure 9:
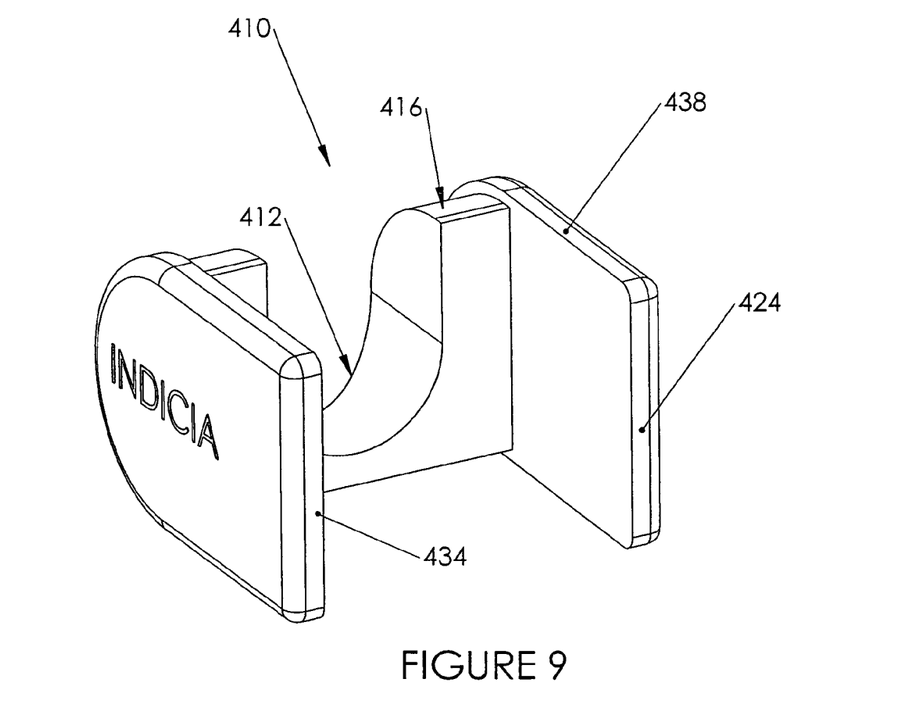
FIG. 9 shows an opposing perspective view of the information ring shown in FIG. 8.

A fourth embodiment of the present invention of an information ring 410 according to the present invention is shown in FIGS. 8 and 9. The information ring 410 is similar to the information ring 210 described above, but with a second indicia portion 434 that is located at the second end 416 of the body 412, and includes an indicia face 436, on which identifying indicia is typically printed. As shown in FIG. 9, the second indicia portion 434 is preferably the same generally elongated shape as the first indicia portion 424.

Figure 10:
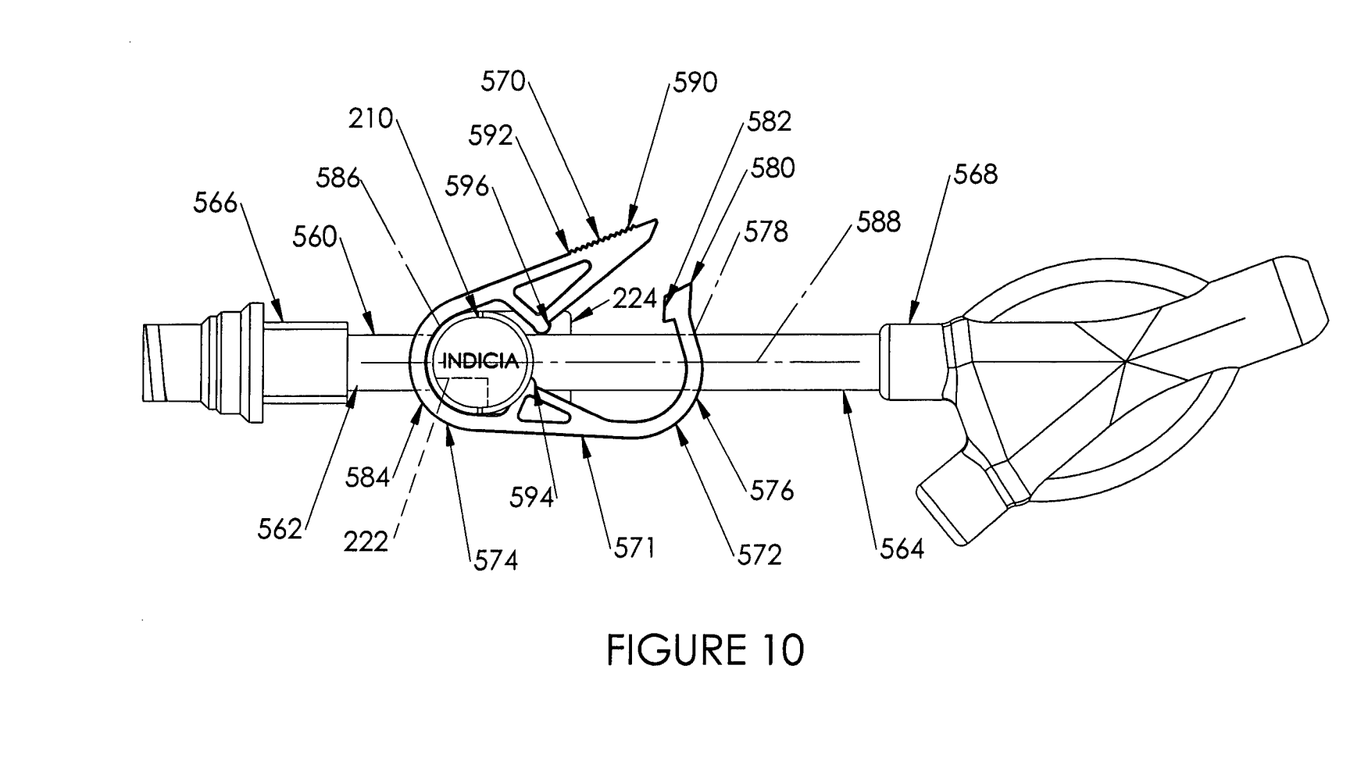
FIG. 10 shows a side view of a catheter assembly incorporating the information ring shown in FIGS. 4 and 5.
Figure 11:
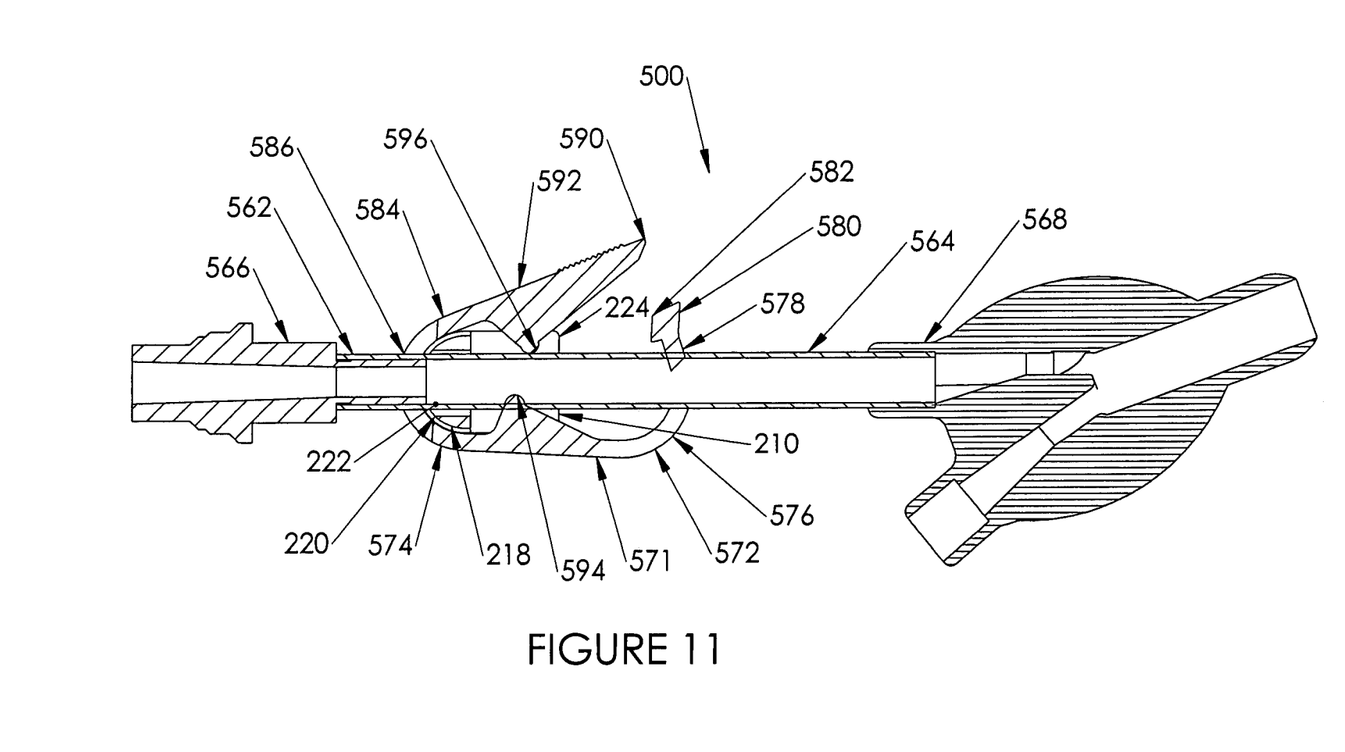
FIG. 11 shows a sectional view of the catheter assembly of FIG. 10.

A catheter assembly 500 that uses an information ring 210, 310, 410 according to any of the above-described second through fourth embodiments is shown in FIGS. 10 and 11. For clarity, only the information ring 210 will be described with reference to the catheter assembly 500, although those skilled in the art will recognize that either embodiment of the information rings 310, 410 may be similarly used in the catheter assembly 500.

As seen in FIGS. 10 and 11, the catheter assembly 500 includes a conduit 560, which is typically a generally circular tube that allows fluid flow between a proximal end 562 and a distal end 564. The conduit 560 is typically an extension tube located at the proximal end of a catheter. A connection device 566, such as a luer, is typically connected to the proximal end 562, and a hub 568 is typically connected to the distal end 564.

The information ring 210 is disposed over the conduit 560 such that the conduit 560 is disposed within the channel 122. A conduit clamp 570, which is well known to those skilled in the art, is also disposed over the conduit 560 and releasably retains the information ring 210 onto the conduit 560. The information ring 210 is sized to fit generally within the conduit clamp 570. The information ring 210 and the conduit clamp 570 are free to translate along the conduit 560 between the first and second ends 562, 564. It is seen that both the first and second ends 214,216 protrude outwardly beyond laterally outwardly facing side edges of the clamp at second end 574 and at first and second clamping portions 594,596, and first and second ends 214,216 extend to peripheral edges that are sized to comprise flanges that partially overlie sufficient portions of the clamp's side edges to maintain the information tin within the interior of the clamp. Also seen in FIG. 11 is that the interconnecting section of the information ring does not impinge on the conduit after assembly and does not interfere with manual movement of locking tab 592 to clamp the tubing at clamping portions 594,596.

Referring to FIGS. 10 and 11, the conduit clamp 570 is shown in an open position. The conduit clamp 570 includes a generally elongated base 571 having a first end 572 and a second end 574. The first end 572 includes a first curved portion 576 having a generally elongated first opening 578 extending therethrough. A free end 580 of the first curved portion 576 includes a locking tang 582. The second end 574 includes a second curved portion 584 having a generally elongated second opening 586 extending therethrough. A line extending through the first and second openings 578, 586 forms a clamp axis 588. A free end 590 of the second curved portion 584 includes a generally elongated locking tab 592. A first clamp member 594 extends from the base 571 between the first and second openings 578, 586 toward the clamp axis 588. A second clamp member 596 extends from the locking tab 592 toward the clamp axis 588. The first and second clamp members 594, 596 are generally offset from each other such that, when the clamp members 594, 596 are biased toward each other, each clamp member 594, 596 engages the conduit 560 such that the conduit 560 is pinched off, preventing fluid flow through the conduit 560. When the locking tab 592 is biased toward the clamp axis 588, the locking tab 592 engages the locking tang 582, securing the clamp 570 and pinching off the conduit 560 via the clamp members 594, 596.

Referring still to FIGS. 10 and 11, the conduit 560 extends through the first and second openings 578, 586 in the conduit clamp 570 along the clamp axis 588. The information ring 210 is disposed such that the conduit 560 extends through the channel 222 of the information ring 210, and the information ring 210 is between the first and second openings 578, 586. The body 212 is disposed such that the rounded second face 220 of the body 212 is loosely engageable against the second curved portion 584 so that the generally rounded second face 220 is nestled in the second curved portion 584. The clamps 594, 596 loosely engage the first face 218, preventing the information ring 210 from axially traversing along the conduit 560 toward the locking tang 582, potentially interfering with the engagement of the clamps 594, 596 with the conduit 560.

The information ring 210 may be inserted onto a conduit assembly 500 that does not initially include an information ring 210. Alternatively, a first information ring 210 according to the present invention may be removed from the conduit assembly 500 without removing either the luer lock 566 or the hub 568 from the conduit 560, and a second information ring 210 may be installed in the conduit assembly 500 in place of the now-removed first information ring 210. The following process will describe only the method for removing a first information ring 210 and replacing a second information ring 210, although those skilled in the art will recognize that the method for only installing an information ring 210 is inherent in the last several steps of the removal and replacement method.

The conduit assembly 500 is grasped and the conduit 560 is drawn through at least one of the openings 578, 586 in the conduit clamp 570 toward the other opening 586, 578 in the conduit clamp 570, such that the conduit 560 between the first and second openings 578, 586 is pulled away from the clamp axis 588. The locking tab 592 may need to be biased away from the locking tang 582 to provide sufficient room to draw out the conduit 560. When the conduit assembly 500 is a catheter assembly, the conduit 560 is a soft, pliable material, allowing the conduit 560 to easily bend. The conduit 560 is bent away from the base 571 of the conduit clamp 570 sufficiently to allow the information ring 210 to be removed from the conduit clamp 570. The conduit 560 is laterally removed from the information ring 210 by pulling the conduit 560 through the channel 222 and out the open end 222*a* of the channel 222.

A new information ring 210 is then inserted into the space between the conduit 560 and the base 571. The conduit 560 is disposed in the open end 222*a* of the channel 222 and retained against the closed end 222*b* of the channel 222. The second face 218 of the body 212 is retained against the second curved portion 584 of the conduit clamp 570. The conduit 560 is then advanced through at least one of the first and second openings 578, 586 so that the conduit 560 extends along the clamp axis 588 through both openings 578 and 586 in the conduit clamp 570. The conduit clamp 570 now releasably retains the information ring 210 on the conduit 560.

Those skilled in the art will recognize that the operation and use of the third and fourth embodiments of the information rings 310, 410 is similar to the operation and use of the second embodiment of the information ring 210 as described above.

Figure 12:
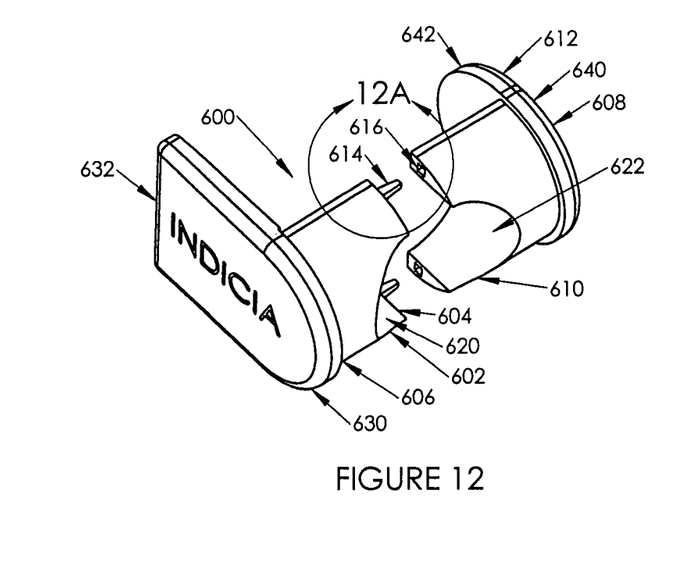
FIG. 12 shows a perspective view of an information ring according to a fifth embodiment of the present invention.
Figure 12A:
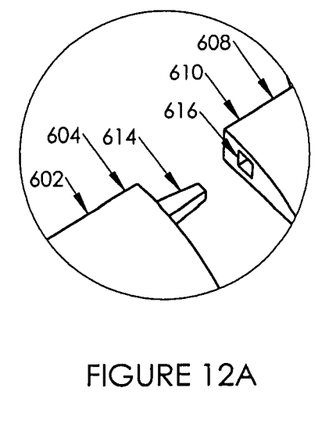
FIG. 12A shows an enlarged view of the connection device on the information ring shown in FIG. 12.
Figure 13:
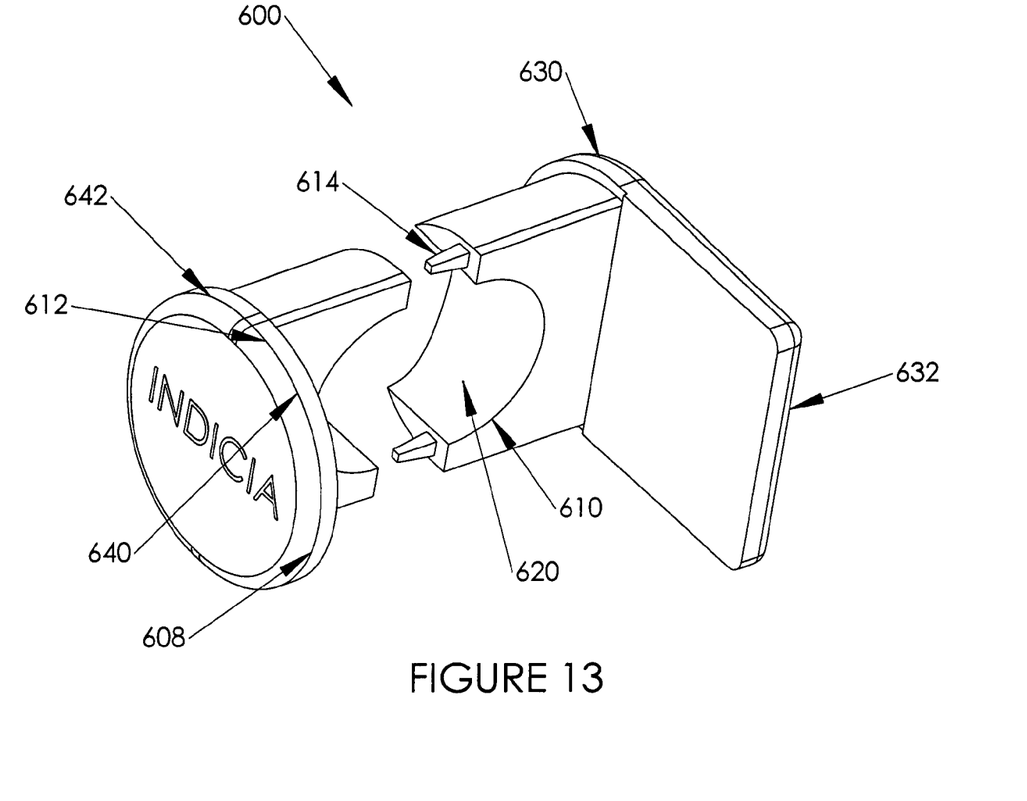
FIG. 13 shows an opposing perspective view of the information ring shown in FIG. 12.

A fifth embodiment of an information ring 600 according to the present invention is shown in FIGS. 12, 12A, and 13. The information ring 600 is comprised of two separate pieces that preferably releasably engage with each other to form a ring having a generally circular opening extending therethrough.

The information-bearing article or ring 600 is comprised of a first connecting or interconnecting portion 602 that has a connecting end 604 and a free end 606, and a second connecting or interconnecting portion 608 that has a connecting end 610 and a free end 612, disposed on first and second body portions 630, 640. One or both of first and second body portions 630,640 have outwardly facing surfaces at least one of which has indicia thereon. The connecting end 604 of the first connecting portion 602 preferably has at least one of a male connector 614 or female connector 616, such as a tab or a slot, respectively, as shown in detail in FIG. 12A. The connecting end 610 of the second connecting portion 608 preferably has at least one of the other of the male connector 614 or the female connector 616, so that, when the first connecting portion 602 and the second connecting portion 608 are brought together, the male connector 614 engages with the female connector 616, releasably securing the first connecting portion 602 and the second connecting portion 608 together. As shown in FIGS. 12, 12A, and 13, the first connecting portion 602 includes the male connector 614 and the second connecting portion 608 includes the female connector 616, although those skilled in the art will recognize that other combinations may be used.

As shown in FIG. 12A, the male connector 614 may be a tapered polygon, such as pyramidal or frusto-pyramidal. The male connector 614 and the female connector 626 allow the first connecting portion 602 and the second connecting portion 608 to be cyclically separated and removed from each other such that the information ring 600 may be removed from a catheter assembly such as the catheter assembly 500 described above, and reused on that or another catheter assembly.

Alternatively, although not shown, the male connector 614 may be other shapes, such as conical, frusto-conical, or any other shape that can engage a mating female connector in a press fit. However, those skilled in the art will recognize that other methods of connecting the first connecting portion 602 and the second connecting portion 608 may be used. For example, the first connecting portion 602 and the second connecting portion 608 may have interlocking male and female connectors (not shown) in a snap-fit engagement, for example, such that, once the male connector is inserted into the female connector, the only way to separate the first connecting portion from the second connecting portion is to destroy at least one of the first connecting portion 602 and the second connecting portion 604, precluding reuse of the information ring 600.

The first connecting portion 602 has a generally semi-circular opening 620, with the connectors 614 of the first connecting portion 602 being located at the connector end 604 on either side of the opening 620. The second connecting portion 608 also has a generally semi-circular opening 622, with the connectors 616 of the second connecting portion 608 also being located at the connector end 610 on either side of the opening 622 such that, when the connector ends 604, 610 of each of the first connecting portion 602 and the second connecting portion 608 are brought together and the male and female connectors 614, 616 are engaged, a generally circular opening is formed. The opening is sized to allow a conduit, such as a catheter extension tube, to be retained inside the opening.

The free end 606 of the first connecting portion 602 has an indicia portion 630 that extends generally orthogonally from the first connecting portion 602. The indicia portion 630 has an indicia face 632 that is disposed distally from the connecting end 604, with indicia being printed on the indicia face 632. The free end 612 of the second connecting portion 608 may also have an indicia portion 640 that extends generally orthogonally from the second connecting portion 608. The indicia portion 640 has an indicia face 642 that is disposed distally from the connecting end 610, with indicia being printed on the indicia face 642.

Preferably, each information ring 210, 310, 410, 600 is constructed from a rigid or a semi-rigid plastic, such as ABS, polyvinyl chloride (PVC), polypropylene, or other suitable material, although those skilled in the art will recognize that the information ring 210, 310, 410, 600 may be made from other materials as well.

Preferably, the material used to construct the information ring 210, 310, 410, 600 is generally at least slightly pliable, to allow manipulation of the information ring 210, 310, 410, 600 without the likelihood of breaking the information ring 210, 310, 410, 600.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method of positioning an information ring onto a catheter assembly comprising:
   positioning a conduit clamp on a conduit having a first end and a second end with a first connector affixed to the first end and a second connector affixed to the second end, wherein the conduit is disposed within openings in the conduit clamp;
   positioning an information ring on the conduit between the first and second connectors, the information ring including a body having a first end and a second end, wherein the body has a first body face extending between the first end and the second end, and a second body face extending between the first end and the second end, and wherein the body has an opening extending therethrough between the first body face and the second body face, and a first indicia portion having a first face extending from the first end of the body of the information ring, wherein the first indicia portion has indicia printed thereon; wherein the step of positioning the information ring on the conduit includes relative lateral movement between the information ring body and the conduit such that the conduit is disposed within the opening between the first body face and the second body face of the information ring; and
   positioning the conduit clamp about the information ring.

2. The method according to claim 1, wherein the opening is a generally U-shaped channel.

3. The method according to claim 2, wherein the body further comprises a first tab extending into the channel.

4. The method according to claim 3, wherein the body further comprises a second tab extending into the channel toward the first tab.

5. The method according to claim 1, wherein the channel has an open portion and an opposing closed portion, and wherein the channel is sized to allow the conduit to be inserted into the open portion and retained against the closed portion.

6. The method according to claim 1, wherein the body is comprised of two portions each having a facing surface so formed to be connected to each other about the medical tubing, the two portions further defined as:
   a first portion having a first connecting end and a first free end, wherein the first connecting end includes at least one of a male connector or a female connector and wherein the first free end has a first face sized to enable indicia to be printed thereon; and
   a second portion having a second connecting end and a second free end, wherein the second connecting end has at least the other of a mating male connector or a mating female connector and wherein the second free end has a second face;
   wherein, when the at least one of the male connector or the female connector is engaged with the at least one of the mating male connector or the mating female connector, a generally circular opening is formed in the ring such that a catheter conduit is sized to fit within the opening.

7. The method according to claim 6, wherein the second face has indicia thereon.

8. The method according to claim 6, wherein the at least one of the male connector or the female connector is engaged with the other one of the mating male connector or the mating female connector with a press fit.

9. The method according to claim 6, wherein the first portion is cyclically removable from and connectable with the second portion.

10. The method according to claim 6, wherein the first and second portions define two pairs of mating male and female connectors with one pair connecting on one side of the opening and the other pair connecting on the opposite side of the opening.

11. The method according to claim 1, wherein the information ring further comprises a second indicia portion at the second end having a second indicia face.

12. The method according to claim 11, wherein the second indicia face of the second indicia portion includes indicia printed on the second indicia face.

13. The method according to claim 11, wherein the second end is generally circular and of similar dimensions to a cross-section of the transverse section.

14. The method according to claim 11, wherein the second indicia portion is generally elongated.

15. The method according to claim 11, wherein the second indicia portion is integral with the body.

16. The method according to claim 1, wherein the first end is generally circular and of similar dimensions to a cross-section of the transverse section.

17. The method according to claim 1, wherein the first indicia portion is generally elongated.

18. The method according to claim 1, wherein the opening is generally circular.

19. The method according to claim 1, wherein the information ring is positioned on the conduit after the conduit clamp is positioned on the conduit.

* * * * *